United States Patent [19]

Wanamaker

[11] Patent Number: 4,841,985
[45] Date of Patent: Jun. 27, 1989

[54] BLOOD DRAWING APPARATUS

[76] Inventor: Thomas Wanamaker, R.R. 2, Box 619, Smithville, Mo. 64089

[21] Appl. No.: 854,171

[22] Filed: Apr. 21, 1986

[51] Int. Cl.⁴ ............................................. A61B 5/00
[52] U.S. Cl. .................................. 128/763; 128/770; 604/240
[58] Field of Search ............... 128/763, 770; 604/205, 604/206, 235, 240, 413

[56] References Cited

U.S. PATENT DOCUMENTS

| D. 240,723 | 5/1966 | Hamilton | D38/12 |
|---|---|---|---|
| 3,159,159 | 12/1964 | Cohen | 128/2 |
| 3,974,832 | 8/1976 | Kruck | 128/221 |
| 4,085,737 | 4/1978 | Bordow | 128/2 |
| 4,123,091 | 10/1978 | Cosentino et al. | 604/240 |
| 4,150,666 | 4/1979 | Brush | 128/2 |
| 4,154,229 | 5/1979 | Nugent | 128/764 |
| 4,155,350 | 5/1979 | Percarpio | 128/764 |
| 4,307,731 | 12/1981 | Kaufman | 128/766 |
| 4,333,478 | 6/1982 | Krieg | 128/764 |
| 4,409,990 | 10/1983 | Mileikowsky | 128/763 |
| 4,418,703 | 12/1983 | Hoch et al. | 128/763 |

FOREIGN PATENT DOCUMENTS 771890 10/1934 France ..................... 128/763

Primary Examiner—Max Hindenburg
Attorney, Agent, or Firm—Michael Yakimo, Jr.

[57] ABSTRACT

A blood sample device for drawing blood from the patient. The device includes a locking mechanism which holds a biased needle assembly in the needle holder during use. Upon release of the locking mechanism, the bias on the needle assembly ejects the same from the holder. Various embodiments of locking mechanism, utilized with and without various bias means, are utilized.

40 Claims, 4 Drawing Sheets

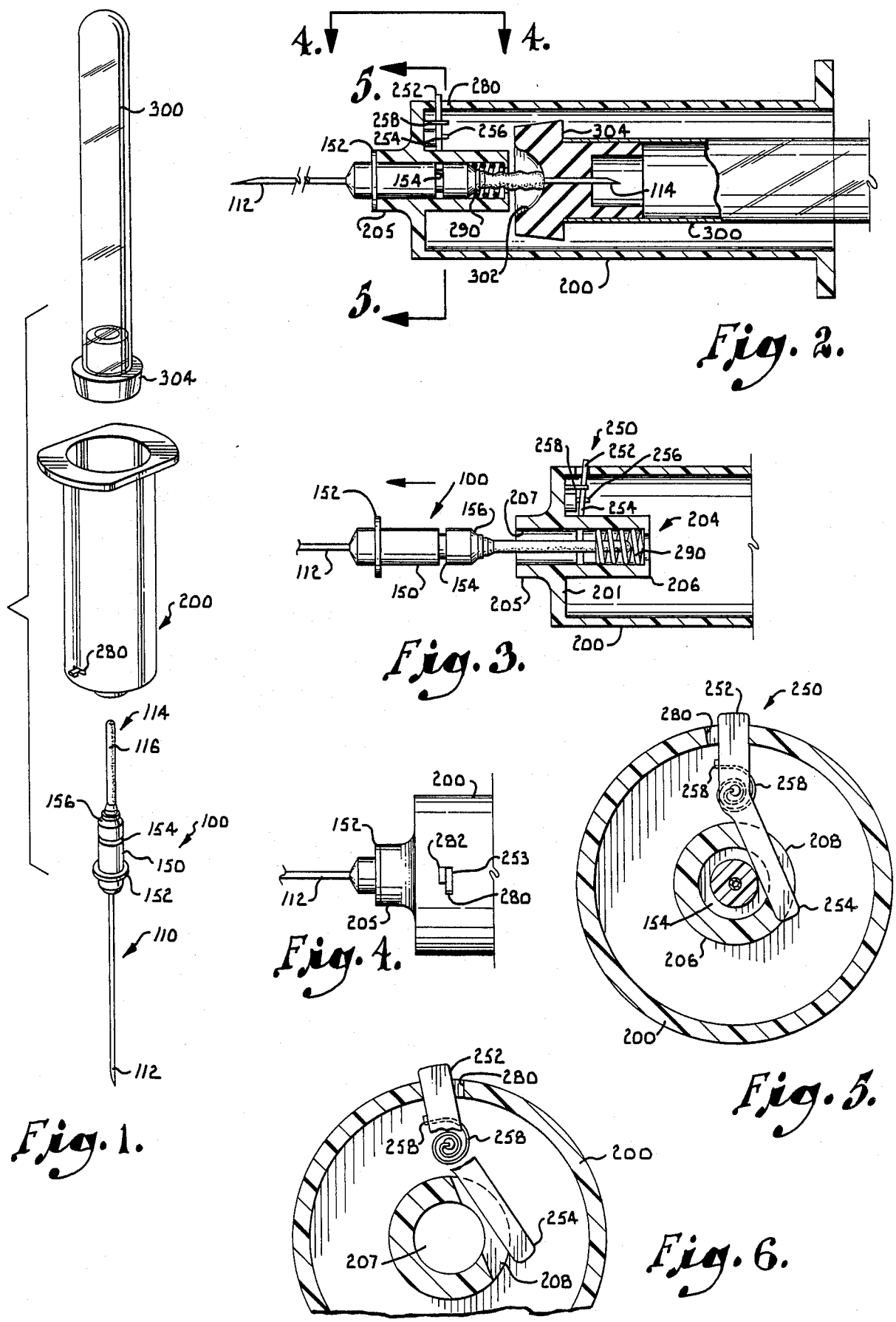

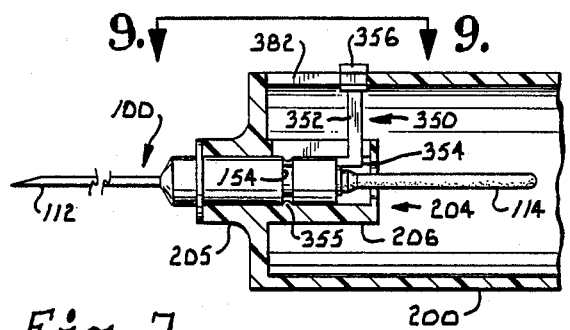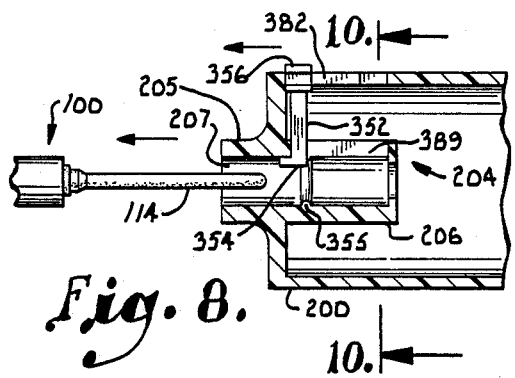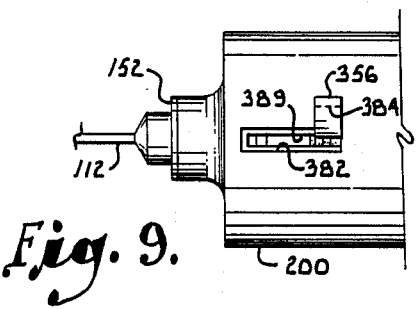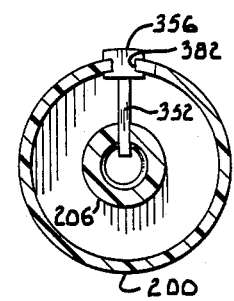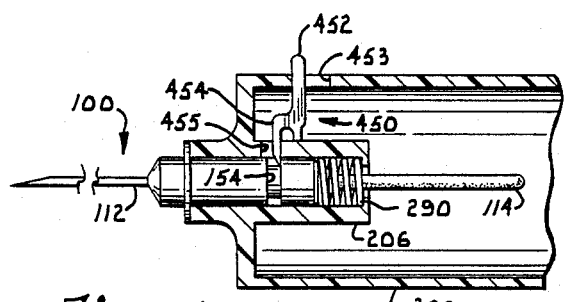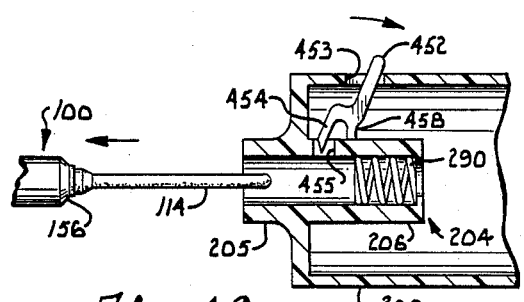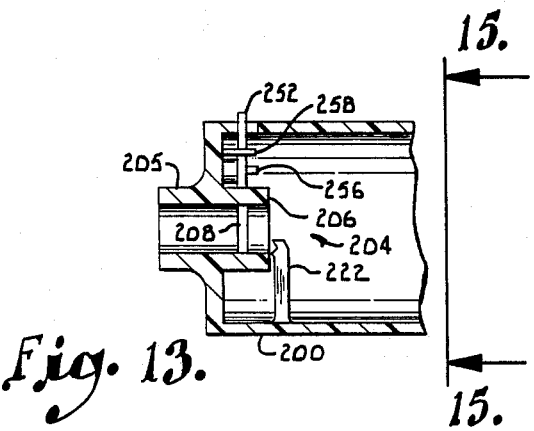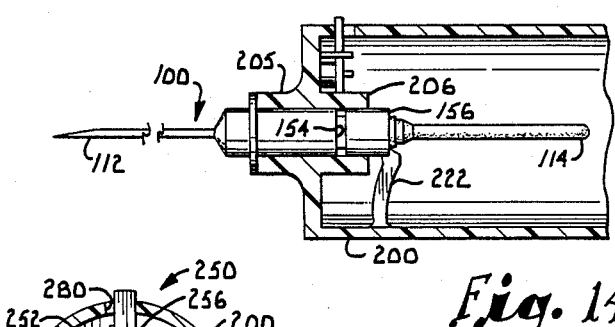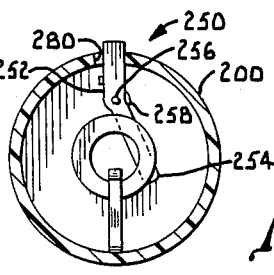

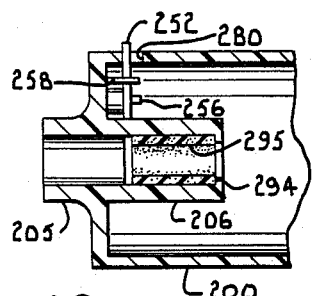
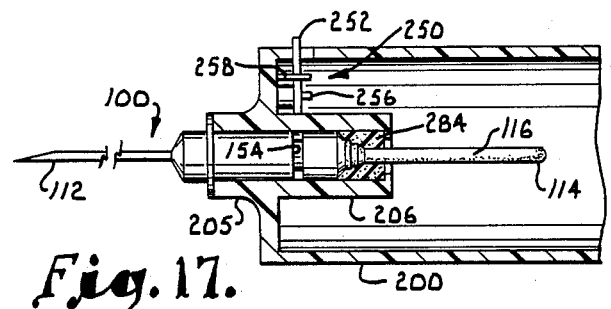
Fig. 16.  Fig. 17.
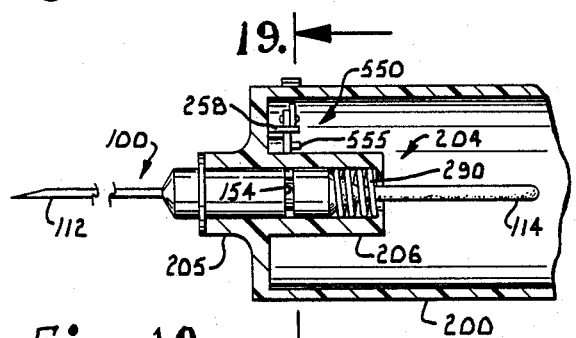
Fig. 18.
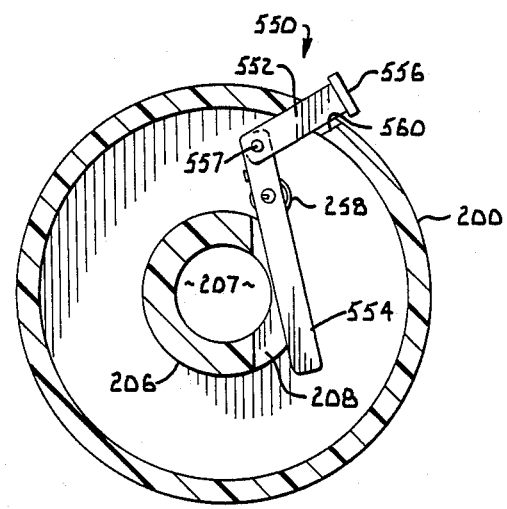
Fig. 20.
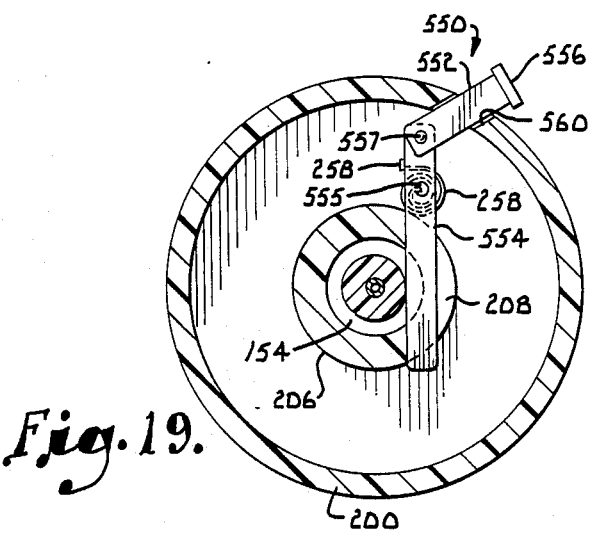
Fig. 19.
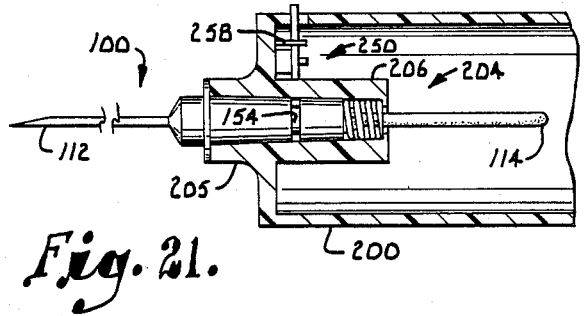
Fig. 21.
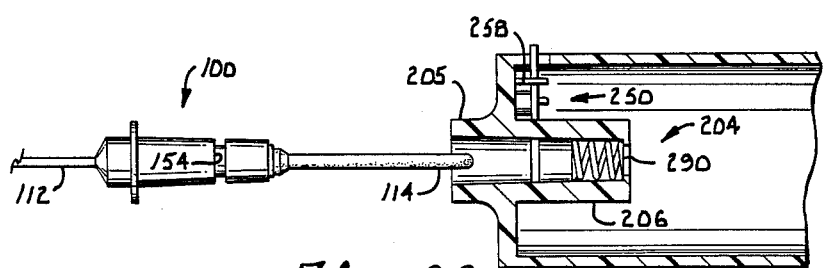
Fig. 22.

BLOOD DRAWING APPARATUS

BACKGROUND OF THE INVENTION

This invention pertains to a blood sampling device and more particularly to apparatus which reduces the possibility of risk of contamination by diseased blood to the user.

The analyses of a patient's blood is an important tool used in diagnosis. The blood is drawn from the patient by the use of various syringe-type apparatus. Blood collection devices utilize a needle inserted into the vein of the patient, i.e. venipuncture, so as to draw the blood through the needle and into an associated collection reservoir.

In light of the recent AIDS problem, attention has been directed to the risk of contamination of the blood drawer/user due to contact with the blood of a diseased patient. Contamination may occur either through the user being punctured by a used needle upon its removal from the blood collection device and/or the splashing of the blood onto the user during such removal.

The use of various blood collection devices are common in the art. One device generally comprises a needle holder, a needle assembly and an evacuated blood collection tube. The needle assembly is threadably engageable with the needle holder and presents a front end for puncturing the vein of the patient and a rear end for insertion into an evacuated collection tube.

The evacuated tube causes the blood to be drawn from the patient, via the venipunctured front end, and discharged into the collection tube from the rear end. As the disposal of the used needle assembly requires manual handling by the user, the possibility of skin puncture and an undesired transfer of diseased blood into the user arises. Also, diseased blood may splash onto the user during removal.

In response thereto, I have invented a needle holder/needle assembly which eliminates the need for the user to manually handle the needle assembly subsequent to blood purging. My now preferred embodiments releasably connects/locks a biased needle assembly with the needle holder and blood collection tube. Subsequent to blood withdrawal, the user operates a locking mechanism so that the biased needle assembly is released/ejected from the needle holder. The released needle assembly may then be directed into a waste receptacle for subsequent disposal. Thus, the user does not manually handle the needle assembly subsequent to its use. I have herein disclosed various embodiments of locking and bias means utilized in connection with my invention.

It is therefor a primary object of this invention to provide for an improved blood collection device which reduces the risk of contamination to users.

Another general object of this invention is to provide for a blood collection device, as aforesaid, which particularly reduces the risk of contamination upon disposal of the utilized needle.

Still another general object of this invention is to provide for a blood collection device, as aforesaid, which precludes the need for the user to manually handle the needle assembly after use.

Another object of this invention is to provide a blood collection device, as aforesaid, which utilizes a needle assembly releasably engageable with a needle holder.

A further object of this invention is to provide a blood collection device, as aforesaid, which utilizes a bias on the needle assembly to urge removal of the needle assembly from the associated needle holder.

Other objects and advantages of this invention will become apparent from the following description taken in connection with the accompanying drawings, wherein is set forth by way of illustration and example, an embodiment of this invention.

BRIEF DESCRIPTION OF THE DRAWINGS

FIG. 1 illustrates an exploded, perspective view of one embodiment of the blood collection device;

FIG. 2 is a medial, sectional view, taken along the medial centerline of the device of FIG. 1, illustrating the elements of FIGS. 1 in position for use;

FIG. 3 is a fragmentary, sectional view of the device, as shown in FIG. 2, illustrating the ejection of the needle assembly from its housing and holder;

FIG. 4 is a side view, taken along lines 4—4 in FIG. 2, illustrating the needle locking assembly and lever in a locked position;

FIG. 5 is a sectional view, taken along lines 5—5 in FIG. 2 and on an enlarged scale, illustrating the biased engagement of the locking lever with the locking slot of the needle assembly;

FIG. 6 is a fragmentary, sectional view, as shown in FIG. 5, illustrating the locking lever in a released position with a portion of a lever arm removed to show the underlying return spring;

FIG. 7 illustrates an alternative, slidable locking lever bearing against the needle assembly as held in place by an annular rim engaging the locking slot of the needle assembly;

FIG. 8 is a fragmentary, sectional view illustrating the movement of the locking lever of FIG. 7 to a released position and concurrent ejection of the needle assembly;

FIG. 9 is a plan view, taken along lines 9—9 in FIG. 7, illustrating the locking lever of FIG. 7 in a locked position;

FIG. 10 is a sectional view, taken along lines 10—10 in FIG. 8, illustrating the relationship of the locking lever with the housing for the needle assembly;

FIG. 11 is a sectional, horizontal view showing an alternative locking structure as maintaining the biased needle assembly within its housing;

FIG. 12 is a sectional view illustrating the structure of FIG. 11 in a released position and the ejected needle assembly from its housing;

FIG. 13 is a fragmentary, sectional view illustrating an alternative embodiment for presenting a bias against the needle assembly as used with the locking lever of FIGS. 1-6;

FIG. 14 is a sectional view illustrating the structure of FIG. 13 offering its bias against an engaged needle assembly;

FIG. 15 is a sectional view, taken along lines 15—15 in FIG. 13, illustrating the relationship of the leaf spring bias of FIGS. 13 and 14 and locking mechanism with the housing of the needle assembly;

FIG. 16 is a fragmentary, sectional view illustrating the use of a compressible material within the housing of the needle assembly for biasing the same;

FIG. 17 is a sectional view illustrating the compression of the FIG. 16 material upon engagement of the needle assembly within its housing;

FIG. 18 is a sectional view illustrating an engaged needle assembly as maintained by the alternative locking lever further illustrated in FIGS. 19 and 20;

FIG. 19 is a sectional view, taken along lines 19—19 in FIG. 18 and on an enlarged scale, illustrating an alternative, pushbutton locking mechanism in an engaged/locking position;

FIG. 20 is a view as in FIG. 19 illustrating the pushbutton locking mechanism in a disengaged/released position;

FIG. 21 is a fragmentary, sectional view illustrating an alternative, tapered housing for receiving a tapered needle assembly therein;

FIG. 22 is a fragmentary, sectional view illustrating the ejection of the needle assembly from the tapered housing;

DESRIPTION OF THE PREFERRED EMBODIMENT

Figure 23:
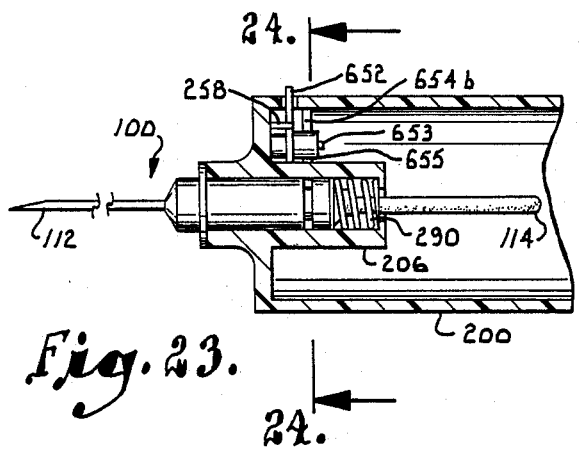
FIG. 23 is a fragmentary, sectional view illustrating an engaged needle assembly as maintained by a cam-type locking mechanism further illustrated in FIGS. 24-25.

Turning more particularly to the drawings, FIG. 1 illustrates a first embodiment of a blood collection device as generally comprising a needle assembly 100, a needle holder 200 and an evacuated sample collection tube 300.

The needle assembly generally comprises a cannula 110 having a front end 112 for venipuncture and a covered 116 rear end 114 for insertion through a membrane 302 of the stopper 304 of tube 300. A removable cover (not shown) encloses the front end 112 of the needle 110 prior to use. An intermediate hub 150 surrounds needle 110 and includes a stop ring 152 and an annular locking slot 154.

The needle holder 200 is generally cylindrical in configuration for receiving the evacuated collection tube 300 therein. Preferrably integral with the holder 200 is a front, exterior boss 205 and a colinear, interior boss 206 which cooperate to present a needle housing generally designated as 204. Bore 207 within housing 204 allows for slidable insertion of the hub 150 and rear end 116 of the needle assembly 100 therein.

A slot 208 within the wall of the interior boss 206 allows for insertion of an arm 254 of locking lever assembly 250 therein. The locking lever assembly 250 includes integral first 252 and second 254 arms rotatably mounted about a pivot pin 256 extending from the interior base 201 of the holder 200. Lever arm 254 is spring-biased 258 into a position extending through slot 208 and into the bore 207. The free end of the arm 252 extends through a slot 280 in the wall of the needle holder 200.

Upon insertion of the needle assembly 100 into bore 207 of housing 204, the cannula rear end 114 extends through the coils of spring 290 and through the membrane 302 of the tube 300 stopper 304. Upon insertion, the cover 116 of the rear cannula end 114 is pushed back so as to expose the rear end 114 of the cannula 110 within the tube 300 as shown in FIG. 2. The rearward projection of the needle assembly 100 through housing 204 is delimited by abutment of stop member 152 with the front edge of boss 205.

Upon insertion, the rear surface 156 of hub 150 compresses the spring 290 located within the housing. Concurrently, the biased 258 second arm 254 engages the annular locking slot 154 surrounding hub 150. This arm 254/slot 154 engagement overcomes the bias offered by the compressed spring 290 against the hub 150 of the needle assembly 100. Such engagement maintains the needle assembly 100 within housing 204 and in a functional position for use.

The front end 112 of the cannula is then inserted by the blood drawer/user into the patient's vein. The evacuated tube 300 draws the blood through the front end 112 of cannula 110 for ultimate discharge into the sample tube 300 via the rear cannula end 114.

Subsequent to drawing the desired blood sample, disposal of the needle assembly 100 is required. The user pushes the tab 253 at the end of the arm 252 out of the notch 282 in the slot 280. (The engagement of a portion of the arm 252 within notch 282 precludes undesirable movement of arm 252 during use of the device.) Subsequent user-movement of arm 252 along slot 280 pivots the biased second arm 254 away from its locking position within the locking slot 154 (FIG. 6). Once disengaged, the bias offered by the compressed spring 290 ejects the needle assembly 100 from the housing 204. Upon user-release of tab 253, the arm 254 is spring 258 biased into its FIG. 5 position. Accordingly, the user need not handle the needle assembly 100 subsequent to blood withdrawal.

FIGS. 7-10 illustrate an alternative embodiment for locking the needle assembly 100 within its housing 204. A slidable lever 350 comprises a first arm 352 and a second arm 354 normal thereto. A tab 356 at the end of the first arm 352 slidably engages an elongated slot 382 in the side of the needle holder 200. The end of arm 352 extends through an elongated slot 389 in the wall of boss 206 so that arm 354 extends into bore 207 of housing 204. Upon insertion of the needle assembly into its functional position (FIG. 7) within housing 204, the locking slot 154 engages an annular rim 355 extending about the interior of the boss 206 of the housing 204. This rim 355/slot 154 engagement maintains the needle assembly 100 in place for use.

As shown in FIG. 9, tab 356 is slidable into a notch 384 of the elongated slot 382. This tab 356/notch 384 relationship maintains the lever assembly 350 in place during use. Subsequent to use, tab 356 is user-slidable along the elongated slot 382 along with the arm 354 along slot 389. The pressure of arm 354 against the rear surface 156 of hub 150 releases the locking rim 155 from the locking slot 154 and subsequently urges the needle assembly 100 from its housing 204.

FIG. 11 illustrates an alternative embodiment of a locking lever 450 for engagement with the locking slot 154. A flexible lever 450 is attached to the boss 206 via post 458 and includes a user-operable arm 452 extending through slot 453 in holder 200. Protrusion of the prong-type locking arm 454 through the slot 455 in boss 206 engages the locking slot 154 of the needle assembly 100 upon its insertion into housing 204. This engagement overcomes the spring 290 bias so as to maintain the needle assembly 100 in place for use. Upon user-operable movement of the arm 452 within slot 453, as shown in FIG. 12, the locking arm 454 is released from the locking slot 154 so that the spring bias 290 ejects the needle assembly 100 from its housing 204.

FIGS. 13-15 illustrates, in connection with locking lever assembly 250, the use of a flexible leaf-type spring 222 bias against the needle assembly 100. The tensioned spring 222 extends from the interior wall of holder 200 and bears against the rear surface 156 of the hub 150 when the needle assembly 100 is inserted into housing 204. The bias offered by the leaf-type spring 222 is overcome by the arm 254/slot 154 combination as shown in FIGS. 1-6 and 15. As such, the leaf spring 222 is urged away from its normal position (FIG. 14). Upon release of the locking lever 250 from slot 154, as above-described, the leaf-type spring 222 returns to its normal position (FIG. 13) so as to urge the unlocked needle assembly 100 from its housing 204. The use of a resilient material for spring 222 will return the same to its FIG. 13 position.

FIGS. 16 and 17 illustrate, in connection with the locking lever assembly 250, the use of a compressible material 294, such as polyurethane, as the bias against the needle assembly 100. The compressible material 294 is shown as inserted into the bore 207 of the housing 204. A bore 295 extends through such material 294 to allow for projection of the rear cannula end 114 therethrough. Upon insertion of the needle assembly 100 within housing 204, the biased 258 arm 254 engages the locking slot 154 and holds the needle assembly in place for use. Concurrently, the material 294 is compressed, as shown in FIG. 17, so as to offer a bias against the needle assembly 100. Subsequent to use, user-operation of the locking lever 250, as above-described, disengages arm 254 from slot 154. Thus, the material 294 expands to its normal position causing ejection of the needle assembly 100 from its housing.

FIGS. 18-20 illustrate a pushbutton-type of locking lever assembly 550 used in connection with spring 290. This assembly 550 comprises a first arm 552 extending through a slot 560 in the needle holder 200 and a second spring-bias 258 arm 554 extending through slot 208 in the interior boss 206. The ends of the responsive arms are pivotally mounted at 557. Arm 554 is further pivotally mounted about pin 555 extending from the base of holder 200. Upon insertion of the needle assembly 100 within housing 204, arm 554 engages locking slot 154 so as to maintain the assembly 100 in place contra the spring 290 bias. Subsequent to use, user-depression of the pushbutton 556 at the end of arm 552 rotates the spring 258 biased arm 554 about pivot point 555 and out of the locking slot 154 (FIG. 20). Upon disengagement, the spring 290 bias ejects the needle assembly 100 from its housing 204.

FIG. 21 illustrates a locking lever 250/spring 290 combination as shown in FIG. 1-5. However, the interior bore 207 of the housing 204 of the needle assembly has been tapered to receive a tapered hub 150' therein. These complementary configurations enhance the slidable action and fit of the needle assembly 100 within housing 204.

Figure 24:
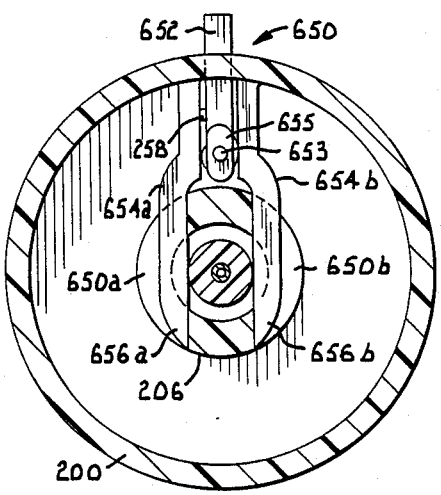
FIG. 24 is a sectional, elevation view, taken along lines 24—24 in FIG. 23 and on an enlarged scale, illustrating the cam-type locking mechanism in an engaged position with the needle assembly.
Figure 25:
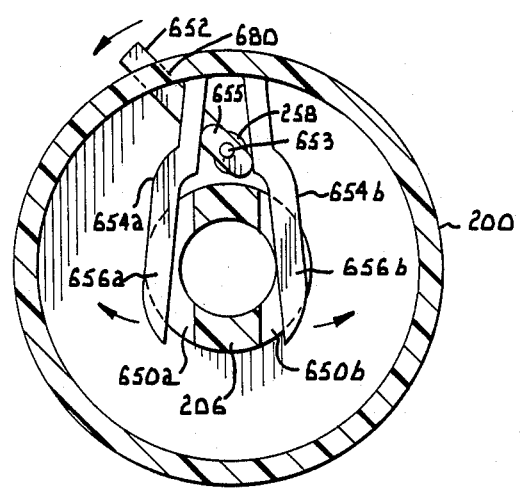
FIG. 25 illustrates the movement of the cam-type locking device of FIG. 24 towards a disengaged position.

FIGS. 23-25 illustrate a cam operated locking lever assembly 650. This assembly 650 comprises a user-operable spring 258-biased locking arm 652 extending through slot 680 in the needle holder 200. The interior end of arm 652 is pivotally mounted at 653 and includes a pivotal, elongated lobe 655 thereon. A pair of flexible, locking arms 654a and 654b extend from the interior of the needle holder 200 and include portions 656a and 656b which normally extend into the bore 207 of housing 204 via slots 650a and 650b. These locking flanges 656a, 656b engage the locking slot 154 of the needle assembly 100 upon insertion into housing 204. Subsequent to use, the arm 652 is user-movable through slot 680, as shown in FIG. 25, which pivots the elongated lobe 655 about pin 653 so as to bear against the arms 654a, 654b. This lobe 655/arm 654 relationship displaces the locking flanges 656a, 656b from the annular slot 154. Once disengaged, the needle assembly 100 is ejected from the housing 204 by the spring-bias 290.

Figure 26:
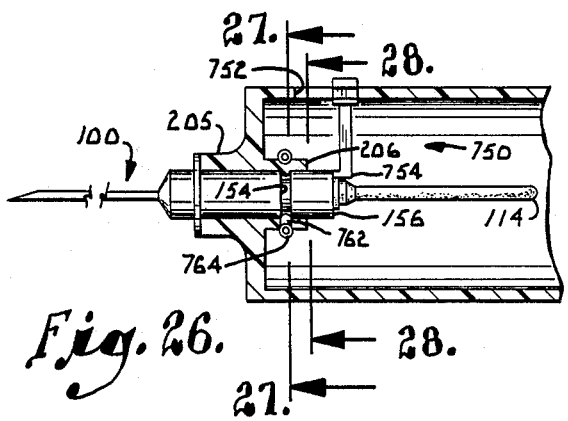
FIG. 26 is a fragmentary, sectional view illustrating an engaged needle assembly, as held in place by an alternative locking ring, as illustrated in FIGS. 27-28, and used in connection with a slidable locking lever illustrated in FIGS. 7-10.
Figure 27:
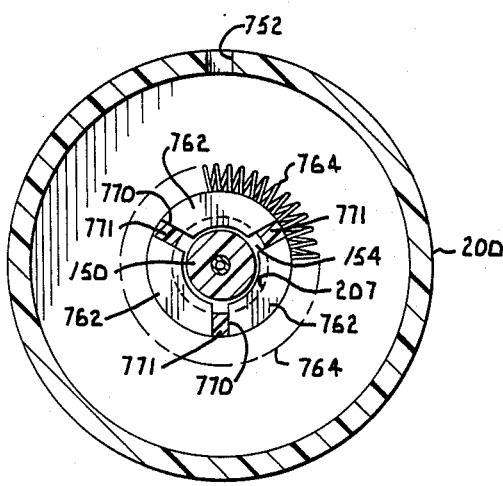
FIG. 27 is a sectional elevation view taken along lines 27—27 in FIG. 26 and illustrating the engagement of the ring with the locking slot of the needle assembly.
Figure 28:
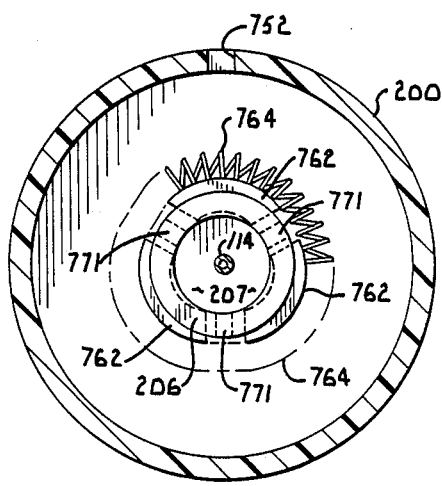
FIG. 28 is a view, taken along lines 28—28 in FIG. 26, illustrating the locking ring in a disengaged/released position and release of the needle assembly from its housing.

FIGS. 26-28 illustrate the use of a locking ring 760 in connection with a lever 750, slidable through slot 752, similar to that shown in FIGS. 9-10. The locking ring 760 includes an interior, three-piece, split ring 762 with an annular spring 764 bias therearound. (Spring 764 partially shown.) The ring 760 is mounted about the exterior of the interior boss 206 such that portions of the split ring 762 are normally biased by spring 764 into the interior bore 207 of the housing 204 via rib-separated 771 annular slot 770 therearound (FIG. 28). Upon insertion of the needle assembly into the housing 204, the hub 150 overcomes the bias of spring 764 so as to urge the ring 762 out of the bore 207 allowing for passage of hub 150 therethrough (FIG. 28). Upon alignment of the locking slot 154 with slot 770, ring 762 extends therein holding the needle assembly 100 in housing 204. (It is noted that spring 764 may surround the housing 204 and annular rim 355 in FIG. 7. By making the housing 204 out of a resilient material, the spring will further bias rim 355 into slot 154.)

Upon locking, arm 754 of lever 750 bears against an end 156 of the needle hub 150. Subsequent to use, the lever 750 is user-slidable along slot 752 causing arm 754 to urge the needle assembly 100 from housing 204. This movement overcomes the bias offered by the spring 764 surrounding the locking ring 762 so as to disengage the three-part ring 762 from the locking slot 154 and release of the needle assembly 100 from its housing 204. Movement of the hub 150 through the housing non-uniformly compresses spring 764 as shown in FIG. 28. Upon release of the needle assembly 100 the spring 764 returns to its relaxed FIG. 27 position.

Although I have shown various particular combinations of locking assemblies/bias means hereinabove, it is understood that other combinations may be utilized.

Also, it is to be understood that while certain forms of this invention have been illustrated and described, it is not limited thereto, except in so far as such limitations are included in the following claims.

Having thus described the invention, what is claimed as new and desired to be secured by Letters Patent is:

1. A fluid collection system comprising:
    a double-ended cannula structure open at both ends and having a bore for passage of fluid therethrough;

a holder having means therein for releasably mounting the cannula structure with one end extending forwardly of said holder for venipuncture and the other end extending rearwardly for coupling with a collection container, said mounting means comprising:

housing means at one end of said holder for receiving a portion of said structure therein with said one cannula end extending forwardly of said housing means in said venipuncture position and said other end extending rearwardly for said coupling with said collection container;

bias means for urging said structure from said housing means after said reception of said structure in said housing means; and user-operable locking means having an operable element exterior of said housing means, said locking means releasably engaging said cannula structure to said housing means after said reception of said structure in said housing means, said engagement overcoming the effect of said bias means in a manner to maintain said respective ends of said cannula structure in said extensions beyond said housing means during use, said user operating said element for disengaging said locking means from said structure, whereupon said bias means urge said cannula structure from said housing means and said holder.

2. The apparatus as claimed in claim 1 wherein said locking means comprises:

female means associated with said cannula structure for receiving a complementary male element;

male means including said male element for engagement with said female means; and means for moving said male element in or out of engagement with said female means, as presented by said operable element exterior of said housing means.

3. The apparatus as claimed in claim 2 wherein said female means comprises:

a hub intermediate the front and rear cannula ends for insertion in said housing means; and a slot in said hub for reception of said complementary male element therein.

4. The apparatus as claimed in claim 3 wherein said moving means comprises:

a first arm having a user-operable end extending from said holder and said housing means; and a second arm associated with said first arm and having said male element therein; and means for pivotally mounting said second arm to said holder in and out of engagement with said slot.

5. The apparatus as claimed in claim 4 wherein said moving means further comprises means for urging said second arm and male element thereon into said engagement with said slot.

6. The apparatus as claimed in claim 5 wherein said urging means comprises a spring member associated with one of said arms in a manner to urge said male element on said second arm into said engagement with said slot.

7. The apparatus as claimed in claim 3 wherein said male means comprises:

a flange member associated with said housing means, said flange engaging said slot upon said reception of said hub in said housing means.

8. The apparatus as claimed in claim 7 wherein said moving means comprises:

a first arm extending into said holder and having a user-operable end;

means for slidably mounting said first arm along said holder; and a second arm associated with said first arm and having an end bearing against said structure upon said reception in said housing means, whereby user movement of said first arm along said holder causes said second arm to bear against said needle structure and urge said flange member from said slot.

9. The apparatus as claimed in claim 3 wherein said male means comprises a prong element engageable with said slot upon said reception of said cannula structure in said housing means.

10. The apparatus as claimed in claim 9 wherein said moving means comprises:

a first arm extending into said holder and having a user-operable end;

means for mounting said first arm in first and second directions relative to said holder;

means for attaching said prong to said first arm in a manner whereby user-movement of said first arm in said first direction removes said prong from said slot; and means for urging said prong in said second direction and into engagement with said slot.

11. The apparatus as claimed in claim 10 wherein said urging means compresses a resilient arm for mounting said first arm, whereby said resilient arm urges said prong into said slot.

12. The apparatus as claimed in claim 3 wherein said moving means comprises:

a first arm having a user-operable end extending from said holder;

a cam element mounted on said first arm;

a second arm extending from said holder and including a first male element for engagement with said slot;

a third arm extending from said holder and including a second male element for engagement with said slot, said cam element being operably engageable with said second and third arms in a manner to displace said male elements from said slot upon movement of said first arm in a selected direction by said user.

13. The apparatus as claimed in claim 3 wherein said male means comprises a ring associated with said housing means, said ring being biased into normal engagement with said slot upon said reception of said cannula structure in said housing means.

14. The apparatus as claimed in claim 13 further comprising a spring element to bias said ring into said engagement.

15. The apparatus as claimed in claim 14 wherein said moving means comprises:

a first arm extending into said holder and having a user-operable end; and a second arm associated with said first arm and having an end bearing against said portion of said structure, whereby user movement of said first arm causes said second arm to bear against said structure and urge said ring from said slot.

16. The apparatus as claimed in claim 1 wherein said bias means comprises resilient means having a normal mode and positioned within said housing means, said resilient means being moved away from said normal position upon said reception of said structure within said housing means whereby movement of said resilient means towards said normal position urges said needle structure from said housing means.

17. The apparatus as claimed in claim 16 wherein said resilient means comprises compressible material positioned within said housing means, said material being urged into a compressed mode upon said reception of said structure withing said housing means.

18. The apparatus as claimed in claim 3 wherein said housing means is configured to receive said hub in a slidable fit therein.

19. The apparatus as claimed in claim 18 wherein said hub presents a configuration complementary to said housing means whereby to enhance said slidable fit therebetween.

20. A fluid collection system comprising:
   a double-ended cannula structure open at both ends and having a bore for passage of fluid therethrough;
   a fluid container holder having means therein for releasably mounting the cannula structure thereto with one cannula end extending forwardly of said holder for venipuncture and the other cannula end extending rearwardly for coupling with said collection container, said mounting means comprising:
   housing means at one end of said holder for receiving a portion of said structure therein with said one cannula end extending forwardly of said housing means in said venipuncture position and said other end extending rearwardly for said coupling with said collection container; and
   user-operable locking means having an user-operable element exterior of said housing means, said locking means releasably engaging said cannula structure to said housing means after said reception of said structure in said housing means, said engagement maintaining said cannula structure in said housing means during use, said user operating said element for disengaging said locking means from said cannula structure after use, whereupon said cannula structure is released from said housing means after use.

21. The apparatus as claimed in claim 20 wherein said locking means comprises:
   female means associated with said cannula structure for receiving a complementary male element;
   male means including said male element for engagement with said female means; and
   means for moving said male element in or out of engagement with said female means, as presented by said operable element exterior of said housing means.

22. The apparaus as claimed in claim 21 wherein said female means comprises:
   a hub intermediate the front and rear cannula ends for insertion in said housing means; and
   a slot in said hub for reception of said complementary male element therein.

23. The apparatus as claimed in claim 22 wherein said moving means comprises:
   a first arm having a user-operable end extending from said holder and said housing means; and
   a second arm associated with said first arm and having said male element therein; and
   means for pivotally mounting said second arm to said holder in and out of engagement with said slot.

24. The apparatus as claimed in claim 23 wherein said moving means further comprises means for urging said second arm and male element thereon into said engagement with said slot.

25. The apparatus as claimed in claim 24 wherein said urging means comprises a spring member associated with one of said arms in a manner to urge said male element on said second arm into said engagement with said slot.

26. The apparatus as claimed in claim 22 wherein said male means comprises:
   a flange member associated with said housing means, said flange engaging said slot upon said reception of said hub in said housing means.

27. The apparatus as claimed in claim 26 wherein said moving means comprises:
   a first arm extending into said holder and having a user-operable end;
   means for slidably mounting said first arm along said holder; and
   a second arm associated with said first arm and having an end bearing against said structure upon said reception in said housing means, whereby user movement of said first arm along said holder causes said second arm to bear against said needle structure and urge said flange member from said slot.

28. The apparatus as claimed in claim 22 wherein said male means comprises a prong element engageable with said slot upon said reception of said cannula structure in said housing means.

29. The apparatus as claimed in claim 28 wherein said moving means comprises:
   a first arm extending into said holder and having a useroperable end;
   means for mounting said first arm in first and second directions relative to said holder;
   means for attaching said prong to said first arm in a manner whereby user-movement of said first arm in said first direction removes said prong from said slot; and
   means for urging said prong in said second direction and into engagement with said slot.

30. The apparatus as claimed in claim 29 wherein said urging means compresses a resilient arm for mounting said first arm, whereby said resilient arm urges said prong into said slot.

31. The apparatus as claimed in claim 22 wherein said moving means comprises:
   a first arm having a user-operable end extending from said holder;
   a cam element mounted on said first arm;
   a second arm extending from said holder and including a first male element for engagement with said slot;
   a third arm extending from said holder and including a second male element for engagement with said slot;
   said cam element being operably engageable with said second and third arms in a manner to displace said male elements from said slot upon movement of said first arm in a selected direction by said user.

32. The apparatus as claimed in claim 22 wherein said male means comprises a ring associated with said housing means, said ring being biased into normal engagement with said slot upon said reception of said cannula structure in said housing means.

33. The apparatus as claimed in claim 32 wherein said ring is operably associated with a spring element to provide for said bias.

34. The apparatus as claimed in claim 30 wherein said moving means comprises:
   a first arm extending into said holder and having a user-operable end; and
   a second arm associated with said first arm and having an end bearing against said portion of said structure, whereby user movement of said first arm causes said second arm to bear against said structure and urge said ring from said slot.

35. The apparatus as claimed in claim 34 further comprising bias means for urging said structure from said housing means upon release of said user-operable locking means from said structure.

36. The apparatus as claimed in claim 35 wherein said bias means comprises resilient means having a normal mode and positioned within said housing means, said resilient means being moved away from said normal position upon said reception of said structure within said housing means whereby movement of said resilient means towards said normal position urges said needle structure from said housing means.

37. The apparatus as claimed in claim 36 wherein said resilient means comprises compressible material positioned within said housing means, said material being urged into a compressed mode upon said reception of said structure within said housing means.

38. The apparatus as claimed in claim 22 wherein said housing means is configured to receive said hub in a slidable fit therein.

39. The apparatus as claimed in claim 38 wherein said hub presents a configuration complementary to said housing means whereby to enhance said slidable fit therebetween.

40. In combination with a fluid vessel the improvement comprising:
   a spout structure having an open bore for passage of fluid therethrough;
   means for releasably mounting the spout structure with one end of the bore extending forwardly for discharge of the fluid from the vessel and the other end extending rearwardly for discharge of the fluid within the vessel, said mounting means comprising:
   housing means for receiving a portion of said structure therein with said forward and rearward extensions:
   bias means for urging said structure from said housing means after said reception in said housing means; and
   user-operable locking means having a user-operable element exterior of said housing means for releasably engaging said structure after insertion of said structure in said housing means, said engagement overcoming said bias means in a manner to maintain said structure in said housing means during use, said user-operable element disengaging said locking means from said structure whereby to release said structure from said housing means after use.

* * * * *

UNITED STATES PATENT AND TRADEMARK OFFICE
CERTIFICATE OF CORRECTION

PATENT NO. : 4,841,985
DATED : June 27, 1989
INVENTOR(S) : Thomas Wanamaker

It is certified that error appears in the above—identified patent and that said Letters Patent is hereby corrected as shown below:

Claim 17, column 9, line 7, change "withing" to --within--

Claim 22, column 9, line 53, change "apparaus" to --apparatus--

Claim 29, column 10, line 32, change "useroperable" to --user-operable--

Claim 34, column 11, line 1, change "30" to --32--

Signed and Sealed this

Nineteenth Day of March, 1991

Attest:

HARRY F. MANBECK, JR.

Attesting Officer

Commissioner of Patents and Trademarks

UNITED STATES PATENT AND TRADEMARK OFFICE
CERTIFICATE OF CORRECTION

PATENT NO. : 4,841,985
DATED : June 27, 1989
INVENTOR(S) : Thomas Wanamaker

It is certified that error appears in the above-indentified patent and that said Letters Patent is hereby corrected as shown below:

Column 9, line 23, delete "said" and substitute --a--.

Signed and Sealed this

Twenty-fourth Day of September, 1996

Attest:

BRUCE LEHMAN

Attesting Officer      Commissioner of Patents and Trademarks